United States Patent
Edgar

(10) Patent No.: US 11,745,000 B2
(45) Date of Patent: *Sep. 5, 2023

(54) DEVICE AND METHOD FOR SELECTIVE APPLICATION OF TOPICAL COMPOSITION USING DYNAMIC THRESHOLD VALUES

(71) Applicant: JOHNSON & JOHNSON CONSUMER INC., Skillman, NJ (US)

(72) Inventor: Albert Durr Edgar, Austin, TX (US)

(73) Assignee: JOHNSON & JOHNSON CONSUMER INC., Skillman, NJ (US)

( * ) Notice: Subject to any disclaimer, the term of this patent is extended or adjusted under 35 U.S.C. 154(b) by 53 days.

This patent is subject to a terminal disclaimer.

(21) Appl. No.: 17/446,912

(22) Filed: Sep. 3, 2021

(65) Prior Publication Data

US 2022/0054811 A1     Feb. 24, 2022

Related U.S. Application Data

(63) Continuation of application No. 16/726,514, filed on Dec. 24, 2019, now Pat. No. 11,110,257.

(Continued)

(51) Int. Cl.
  *A61M 35/00*   (2006.01)
  *G16H 50/20*   (2018.01)
  *A61B 5/00*   (2006.01)

(52) U.S. Cl.
  CPC ........... *A61M 35/003* (2013.01); *A61B 5/004* (2013.01); *A61B 5/444* (2013.01); *G16H 50/20* (2018.01); *A61M 2205/3306* (2013.01)

(58) Field of Classification Search
  CPC ........ A61M 35/003; A61M 2205/3306; A61B 5/004; A61B 5/444; A61B 5/0064;

(Continued)

(56) References Cited

U.S. PATENT DOCUMENTS 8,007,062 B2  8/2011 Edgar et al.
8,027,505 B2  9/2011 Edgar et al.
(Continued)

FOREIGN PATENT DOCUMENTS

WO   WO 2007/022095 A1   2/2007
WO   2010/004565 A2   1/2010
(Continued)

OTHER PUBLICATIONS

International Search Report and Written Opinion dated Nov. 16, 2021 in corresponding International Application No. PCT/US2021/071079.

(Continued)

*Primary Examiner* — Howard D Brown, Jr.
(74) *Attorney, Agent, or Firm* — Wan Chieh Lee; Haug Partners LLP

(57) ABSTRACT

A device and method for selectively applying a composition a treatment surface (e.g., skin) to impart an aesthetically pleasing appearance to the surface. The device may include a detector for obtaining image data corresponding to an image of an area of skin. The device may also include an applicator for selectively applying a fixed amount of the composition to the skin to a location within the area of skin as determined by the device. The fixed amount is selected to reduce the artifact magnitude by a predetermined coverage level when applied to the skin. The device may include a processing arrangement for receiving image data from the detector, determining an artifact magnitude of the location based on the image data, comparing the artifact magnitude to a threshold, and directing the applicator to apply the composition to the skin when the artifact magnitude is above the threshold.

19 Claims, 7 Drawing Sheets

Related U.S. Application Data

(60) Provisional application No. 62/785,452, filed on Dec. 27, 2018.

(58) Field of Classification Search
CPC .... A61B 5/4836; A61B 5/0036; G16H 50/20; A45D 34/04; A45D 44/005; A45D 2044/007; G06T 7/0012; G06T 7/11; G06T 2207/30088; G06T 2207/30204
See application file for complete search history.

(56) References Cited

U.S. PATENT DOCUMENTS

| | | | |
|---|---|---|---|
| 8,103,061 B2 | 1/2012 | Payonk et al. | |
| 8,942,775 B2 | 1/2015 | Edgar et al. | |
| 9,020,184 B2 | 4/2015 | Edgar | |
| 9,247,802 B2 | 2/2016 | Edgar et al. | |
| 9,449,382 B2 | 9/2016 | Edgar et al. | |
| 9,462,872 B2 | 10/2016 | Edgar | |
| 10,092,082 B2 | 10/2018 | Edgar et al. | |
| 10,486,174 B2 | 11/2019 | Edgar et al. | |
| 10,553,006 B2 | 2/2020 | Iglehart et al. | |
| 11,090,474 B2 | 8/2021 | Edgar | |
| 11,110,257 B2 | 9/2021 | Edgar | |
| 11,535,603 B1 * | 12/2022 | DeWitt | A61P 35/00 |
| 2007/0035815 A1 | 2/2007 | Edgar et al. | |
| 2008/0192999 A1 | 8/2008 | Edgar | |
| 2009/0025747 A1 | 1/2009 | Edgar et al. | |
| 2013/0302078 A1 | 11/2013 | Edgar | |
| 2017/0078584 A1 | 3/2017 | Won | |
| 2019/0080451 A1 | 3/2019 | Iglchart et al. | |
| 2020/0107715 A1 | 4/2020 | Dana et al. | |
| 2021/0046296 A1 * | 2/2021 | Binner | A61B 5/0077 |
| 2022/0054811 A1 * | 2/2022 | Edgar | A61B 5/444 |
| 2022/0401514 A1 * | 12/2022 | Schuch | A61K 45/06 |

FOREIGN PATENT DOCUMENTS

| | | |
|---|---|---|
| WO | 2010/145669 | 12/2010 |
| WO | 2012/103048 A2 | 8/2012 |
| WO | 2015/161009 A1 | 10/2015 |
| WO | 2015/191824 | 12/2015 |
| WO | WO 2020/139890 A1 | 7/2020 |

OTHER PUBLICATIONS

International Preliminary Report on Patentability dated Feb. 7, 2023 in corresponding International Application No. PCT/US2021/071079.

International Search Report and Written Opinion dated Mar. 23, 2022 in corresponding International Application No. PCT/US2021/061226.

* cited by examiner

DEVICE AND METHOD FOR SELECTIVE APPLICATION OF TOPICAL COMPOSITION USING DYNAMIC THRESHOLD VALUES

PRIORITY CLAIM

This application is a Continuation Application of U.S. patent application Ser. No. 16/726,514 filed on Dec. 24, 2019; which claims priority to U.S. Provisional Application Ser. No. 62/785,452 filed Dec. 27, 2018, the entire contents of the above-identified application(s)/patent(s) is hereby incorporated by reference herein.

FIELD OF INVENTION

The present invention relates to devices and methods for selectively applying a composition onto a treatment surface, such as a keratinous surface, (e.g., the skin, hair, or nails), or enamel (e.g., teeth) of a user. More specifically, the invention relates to devices and methods for selectively applying a topical composition (e.g., a cosmetic composition or a skin treatment composition) to reduce appearance of undesirable skin features and enhance the aesthetic appearance of skin.

BACKGROUND

Manual application of topical compositions is often imprecise. For example, the heavy application of a foundation base for makeup may cause an undesirable, caked-on appearance. In addition, applying materials over large portions of the skin may waste a large portion of the material, without providing noticeable improvement in aesthetic appearance. Furthermore, the material may form a continuous film over large portions of skin, which may impart an undesirable and unnatural appearance and/or may cause a displeasing, less natural feel for the skin bearing the layers of cosmetic composition. Such a continuous film over large portions of skin may also decrease breathability of the skin and increase exposure of the skin to the topical material, which can increase the surface area of skin exposed to potential allergens and therefore, increase the risk that a user may have undesired or allergic reactions to the topical material.

SUMMARY OF THE INVENTION

One exemplary embodiment of the present invention is directed to a method for selectively applying a composition (e.g., a topical composition or a cosmetic) to a treatment surface, for example, the skin of a user's face. The composition may comprise, for example, a reflectance modifying agent, such as titanium dioxide. The method comprises: (i) obtaining, by a detector arrangement, image data corresponding to an image of an area of the treatment surface; (ii) analyzing, by a processing arrangement, the image data to determine a magnitude of an artifact (a location whose appearance generates an undesired visual effect) within the imaged area; (iii) comparing, by the processing arrangement, the artifact magnitude of the location to a predetermined threshold value; and (iv) applying, by an applicator arrangement, an amount of the composition to locations at which the artifact magnitude is above the predetermined threshold value. The amount applied by the applicator arrangement may be variably selected by the processing arrangement or may be a predetermined fixed amount. The fixed amount of composition is selected to reduce the artifact magnitude by a predetermined coverage level when applied to the treatment surface. The predetermined threshold value may also be selected to exceed the predetermined coverage level of artifact reduction imparted by the fixed amount of the composition when applied to the treatment surface. In one exemplary embodiment, the artifact magnitude is determined based on a reflectance of the treatment surface detected in the image. In certain embodiments, the artifact magnitude is determined as a percentage of a total intensity of light reflectance of an imaged area of treatment surface comprised of those spatial frequency components attributable to artifacts (intensity of spatial frequency components generating an undesired visual effect). More particularly, the artifact magnitude may be determined as a percentage of light reflectance of a location within the imaged area of the treatment surface that comprises spatial frequency components within middle spatial frequencies for the imaged area.

In some embodiments, the method further comprises (v) repeating steps (i) through (iv) for a next area of the treatment surface until a predetermined condition has been met; (vi) adjusting, by the processing arrangement, the predetermined threshold value to a second value lower than the previous predetermined threshold value but higher than a level of artifact reduction imparted by application of the fixed amount of the composition; and (vii) repeating steps (i) through (iv) for a further area of the treatment surface using the adjusted predetermined threshold value. The predetermined condition may be met by receiving manual input from a user via a user interface or may be met when a deposition rate of the applicator arrangement falls below a predetermined rate. In other embodiments, the method may further comprise (iv) adjusting, by the processing arrangement, the predetermined threshold value based on a deposition rate of the applicator arrangement; and (v) repeating steps (i) through (iv) using the adjusted predetermined threshold value for a next area of the treatment surface. The predetermined threshold value may be adjusted to maintain the deposition rate of the applicator arrangement substantially constant.

A handheld device for selectively applying a composition to a treatment surface is also described. The composition may, for example, comprise a reflectance modifying agent. The device comprises a detector arrangement configured to obtain image data corresponding to an image of an area of the treatment surface. In some embodiments, the detector arrangement comprises a light source for delivering light to the region of the treatment surface, and a sensor for detecting light reflected from the area of the treatment surface to obtain the image data. The device also comprises an applicator arrangement configured to apply a fixed amount of the composition to a location within the imaged area as selectively determined by the device based on analysis of the image data. The fixed amount of composition may be selected to reduce the artifact magnitude by a predetermined coverage level when applied to the treatment surface. The device further comprises a processing arrangement receiving the image data from the detector arrangement and analyzing the image data to identify and locate artifacts based on the image data by determining an artifact magnitude at the location of the artifact on the treatment surface (i.e., identifying one or more frexels to which the composition is to be applied). The processing arrangement compares the artifact magnitude to a predetermined threshold value and directs the applicator arrangement to apply the fixed amount of the composition to only those locations at which the artifact magnitude is above the predetermined threshold value. The predetermined threshold value may, for example, be selected to exceed the level of artifact reduction imparted by application of the fixed amount of the composition to the treatment surface. In certain embodiments, the artifact magnitude is determined based on a level of reflectance of the treatment surface detected in the image. More particularly, the artifact magnitude may be determined as a percentage of light reflectance of a location within the imaged area of the treatment surface that comprises spatial frequency components within middle spatial frequencies.

In some embodiments, the processing arrangement is further configured to adjust the predetermined threshold value to a second value when a predetermined condition has been met (e.g., after application of the composition to selected locations has reduced the artifact magnitude at these locations). The second value in these embodiments is lower than the previous predetermined threshold value and higher than the level of artifact reduction imparted by application of the fixed amount of the composition to the treatment surface. The predetermined condition may be met when a deposition rate of the applicator arrangement falls below a predetermined rate indicating that fewer locations are being detected having an artifact magnitude above the previous threshold level. In other embodiments, the processing arrangement is configured to adjust the predetermined threshold value based on a deposition rate to maintain a desired rate of deposition.

These and other aspects of the invention will become apparent to those skilled in the art after a reading of the following detailed description of the invention, including the figures and appended claims.

DETAILED DESCRIPTION

Figure 1:
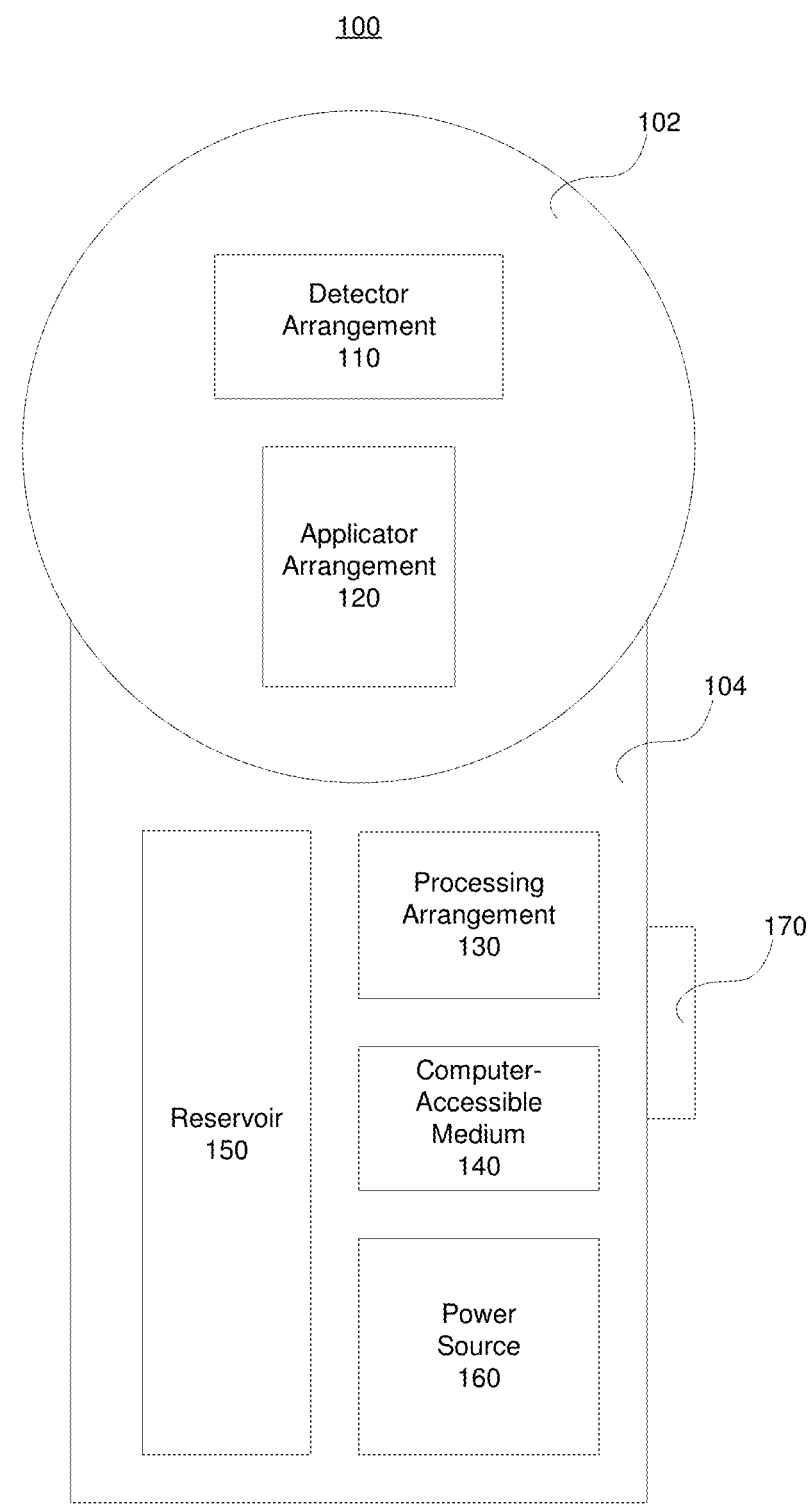
FIG. 1 shows a block diagram of an exemplary device for selectively applying a composition to the skin of a user, according to an exemplary embodiment of the present application.

The term "frexel" as used herein refers to a small pixel-like region of skin, which may correspond to a single large pixel or a small number of pixels in a digitally obtained image of the corresponding portion of skin. For example, a frexel may correspond to a skin area having an average diameter from about 1/15 to about 1/5 inch.

The term "middle spatial frequencies" as used herein is explained further below. For example, image data corresponding to an image of the skin can capture light reflectances extending over a range of spatial frequencies, which measures the level of detail present in an image over a distance across the skin observed by a detector (e.g., a camera) that generates the image data. Spatial frequency may be measured by the number of periodic features, e.g., described as a periodic sine-wave pattern corresponding to cycles of alternating dark and light stripe patterns, within an image over a distance across the skin observed by the detector. The spatial frequency of an image may be calibrated and/or normalized based on a distance from which the skin is imaged by the detector. It is noted that spatial frequency, as used herein, does not measure a wavelength or color of light, but instead refers to a spatial wavelength of the structure of the details of the skin captured by the detector in the image. Data corresponding to an image in a spatial domain (e.g., in the form of pixels or frexel) can be processed by a computer processor using a Fourier transform function to obtain data for the image in the spatial frequency domain. This spatial frequency domain relates to an optical resolution of the image captured, which is distinct from a wavelength or color of light. As would be understood by those skilled in the art, the spatial frequency components of the image may generally be separated into three different categories, including (1) high spatial frequencies, (2) middle spatial frequencies, and (3) low spatial frequencies, using any suitable methods for image analysis, e.g., Fourier transform, filtering, etc. As would be understood by those skilled in the art, spatial frequency components having high spatial frequencies correspond to light reflectance in the image that contribute to the appearance of sharp edges and small details within the image. For example, for an image of skin, the spatial frequency components having high spatial frequencies correspond to features that appear to be small, natural variations in the skin, such as those derived from the genetic code of the person, e.g., pores, hair, follicles, cells, iris of the eye, etc. Low spatial frequencies correspond to light reflectances in the image that contribute to the broad visual appearance such as, for example, the color of larger features such as, for example, the nose, cheeks, etc. The remaining spatial frequency components between the low and spectral frequencies are referred to as the middle spatial frequencies.

The range of middle spatial frequencies may be determined relative to the image captured. For example, the range of middle spatial frequencies for an area of facial skin may be different from the range of middle spatial frequencies for an area of the skin on a leg. The range of middle spatial frequencies may also depend on the underlying skin tone of the skin imaged. In one example, the middle spatial frequencies for human skin can range from about 0.03 cycles/mm to about 1.5 cycles/mm, or more specifically from about 0.05 cycles/mm to about 1.0 cycles/mm and, even more specifically, from about 0.07 cycles/mm to about 0.5 cycles/mm.

The present application provides a device and method for selectively applying a composition to a treatment surface. It is contemplated that the composition may be applied to any suitable treatment surface, such as, an interface between a biological surface and the external environment (e.g., air), in particular, a topical surface. Suitable biological surfaces may include keratinous surfaces (such as, but not limited to, surfaces of the skin, hair, and/or nails), and enameled surfaces (e.g., a surface of a tooth). Preferably, the treatment surface is that of a mammal or a human. Although exemplary embodiments are discussed herein relating to the skin, it is contemplated that the device and method of the present application may be used to selectively apply any suitable composition, in particular, a topical composition to a treatment surface. More particularly, the present application provides a device and method for selectively applying a composition to a surface of the skin of a user to alter or reduce the appearance of undesirable features (artifacts), e.g., scars, wrinkles, blemishes, freckles, sun damage, age spots, etc. while reducing a total amount of composition used. The device and method of the present application may receive image data corresponding to an image of an area of the skin and analyze the image data to identify and locate one or more frexels to which the composition is to be selectively applied. Therefore, the selective application of a composition according to the present application reduces waste and may create a more natural-looking appearance of the skin as less of the skin is covered by the composition than is generally the case with the manual application of a topical composition.

The device and method of the present application may be used to apply a composition to the skin, such as, for example, the skin of the face. The composition to be applied to the skin may comprise, for example, any suitable cosmetic ingredients for modifying an appearance of the skin, such as, for example, an opaque substance, a tinted cosmetic, or any other suitable compositions for enhancing the appearance of skin. The composition may also comprise ingredients such as a moisturizer for hydration, a carrier, or a benefit agent (e.g., a beneficial compound/composition/extract or an active ingredient) for treating and/or ameliorating a skin condition, e.g., acne, hyperpigmentation, eczema, hives, vitiligo, psoriasis, rosacea, warts, shingles, cold sore, pigmentation and tone, redness/oxidative skin stress, wrinkles, brightening, sagging/elasticity, etc. Exemplary embodiments of benefit agents that may be incorporated into the composition are further described below.

A non-limiting list of useful hydrating active benefit agents includes hyaluronic acid, and humectants. The hyaluronic acid may be linear, cross-linked, or a mixture of linear and cross-linked hyaluronic acid. It may be in a salt form, such as sodium hyaluronate. A humectant is a compound intended to increase the water content of the top layers of skin (e.g., hygroscopic compounds). Examples of suitable humectants include, but are not limited to, glycerin, sorbitol or trehalose or a salt or ester thereof.

A non-limiting list of useful benefit agents for acne includes benzoyl peroxide, retinoids including retinol, retinal, retinoic acid, retinyl acetate, and retinyl palmitate, hydroxy acids include, but are not limited to, glycolic acid, lactic acid, malic acid, salicylic acid, citric acid, and tartaric acid, sulfur, Zinc PCA (Zinc Pyrrolidone carboxylic acid), Allantoin (5-ureidohydantoin), Rosemary, 4-hexylresorcinol, N-acetyl glucosamine, gluconolactone, niacinamide, azelaic acid, and resveratrol.

A non-limiting list of useful pigmentation active benefit agents includes resorcinols, such as niacinamide, 4-hexyl resorcinol, curcuminoids (such as Sabiwhite (Tetrahydrocurcumin), phytic acid, resveratrol, soybean *Glycine soja* oil, gluconolactone, azelaic acid, and retinoids including retinol, retinal, retinoic acid, retinyl acetate, and retinyl palmitate, enzymes such as laccase, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, *Chamomilla* extract, allantoin, opacifiers, talcs and silicas, zinc salts, and the like. Examples of suitable tyrosinase inhibitors include but, are not limited to, Vitamin C and its derivatives, Vitamin E and its derivatives, Kojic Acid, Arbutin, resorcinols, hydroquinone, Flavones e.g., Licorice flavanoids, Licorice root extract, Mulberry root extract, *Dioscorea coposita* root extract, *Saxifraga* extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkyl-resorcinols such as 4-butyresorcinol (rucinol), 4-hexylresorcinol, phenylethyl resorcinol, 1-(2,4-dihydroxyphenyl)-3-(2,4-dimethoxy-3-methylphenyl)-Propane and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative A non-limiting list of useful redness/antioxidant active benefit agents includes water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, propolis and extracts of feverfew. By "extracts of feverfew," it is meant extracts of the plant "*Tanacetum parthenium*," One particularly suitable feverfew extract is commercially available as about 20% active feverfew.

A non-limiting list of useful wrinkle active benefit agents includes N-acetyl glucosamine, 2-dimethylaminoethanol, copper salts such as copper chloride, peptides like argireline, syn-ake and those containing copper, coenzyme Q10, dill, blackberry, princess tree, *Picia anomala*, and chicory, resorcinols, such as 4-hexyl resorcinol, curcuminoids and retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid.

A non-limiting list of useful brightening active benefit agents includes Vitamin C and its derivatives such as Ascorbic Acid 2-Glucoside, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid.

A non-limiting list of useful benefit agents for sagging skin includes blackberry extracts, cotinus extracts, feverfew extracts, extracts of *Phyllanthus niruri* and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof.

Additional skin benefit agents or actives may include those actives listed in the following paragraphs. While some of these actives may have been listed above, they are included below to ensure a more robust listing.

Examples of suitable additional benefit agents include: skin lightening agents, darkening agents, anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like. Examples of various suitable additional cosmetically acceptable actives include UV filters such as but not limited to avobenzone (Parsol 1789), bis-disulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as oat, aloe vera, Feverfew, Soy, Shiitake mushroom extracts, and derivatives and mixtures thereof.

Examples of suitable skin lightening benefit agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, *Chamomilla* extract, allantoin, opacifiers, talcs and silicas, zinc salts, and the like.

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulbeny root extract, *Dioscorea coposita* root extract, *Saxifraga* extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkyl-resorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, *Portulaca* extract, Licochalcone, chalcone, 2,2'-dihydroxy chalcone, *Primula* extract, propolis, and the like.

In some preferred embodiments, useful benefit agents for acne include, but are not limited, salicylic acid, Zinc PCA (Zinc Pyrrolidone carboxylic acid), Allantoin (5-ureidohydantoin), Rosemary, 4-hexylresorcinol, N-acetyl glucosamine, gluconolactone, niacinamide, azelaic acid, and resveratrol.

In some preferred embodiments, a list of useful pigmentation active benefit agents includes tetrahydrocurcumin, phytic acid, resveratrol, soybean *Glycine soja* oil, gluconolactone, laccase, 4-hexyl resorcinol, N-acetyl glucosamine, gluconolactone, niacinamide, azelaic acid, and resveratrol.

In some preferred embodiments, a list of useful active benefit agents includes to simultaneously treat acne and pigmentation includes 4-hexyl resorcinol, N-acetyl glucosamine, gluconolactone, niacinamide, azelaic acid, and resveratrol.

In one particular embodiment, the composition comprises one or more reflectance modifying agents (RMAs) (any component useful for altering reflectance of the skin). For example, suitable RMAs may include inks, dyes, pigments, bleaching agents, chemically altering agents and other substances that may be used to alter the reflectance of the skin. Some suitable RMAs may include a transparent RMA, such as a dye or a diluted pigment. Other suitable RMAs may include an opaque RMA having high refractive index particles. In particular, the high refractive index particles may comprise particles having a refractive index of 2.0 or greater. In one specific example, the RMA may comprise particles of titanium dioxide. Specifically, the titanium dioxide particles may be uniformly distributed and/or suspended in the cosmetic composition.

FIG. 1 shows a block diagram of an exemplary device 100 for selectively applying a composition to the skin. The device 100 is preferably sized and shaped as a hand-held device including a handle portion 104 designed to be held within a palm of the user's hand and a head portion 102. The handle portion 104 of the device 100 has an elongated shape defining a cavity housing other components therein. In some embodiments, the handle portion 104 is sized and shaped to be held within the palm of the user's hand. In other embodiments, the handle portion 104 is sized and shaped to be held by the finger tips.

In use, the head portion 102 is placed over an area of skin to be treated and image data corresponding to an image of the area of skin is obtained and analyzed to identify areas (if any) within the imaged area to which a composition housed in the device 100 is to be applied. For example, the image data may be analyzed to identify frexels within the imaged area to which the composition is to be applied. During use, the device 100 may be utilized to image a plurality of different areas of skin. For example, the head portion 102 may be moved across a surface of the skin allowing the device 100 to continuously image (at any desired frame rate) different areas of the skin to obtain image data, analyze the image data to identify, based on a quantitative analysis of the image data, artifacts whose appearance the user wants to minimize or alter, and selectively apply a composition to these artifacts. More particularly, the head portion 102 may be moved back and forth across the surface of the skin in multiple passes to allow the device 100 to review previously treated areas to detect artifacts which were missed or incompletely addressed and apply the composition to identified artifacts on the skin as will be explained further below.

The head portion 102 of the device 100 according to this embodiment comprises a detector arrangement 110 obtaining image data corresponding to an image of an area of skin, so that the image data can be analyzed by a processing arrangement 130 to detect artifacts within the imaged area. The head portion 102 of this embodiment also comprises an applicator arrangement 120 for applying the composition to portions of the skin (frexels) at which the artifacts are detected. For example, the device 100 may capture an image of an area of skin, and the image may be subsequently processed by a processing arrangement 130 to identify frexels that could benefit visually by being altered by the application of a composition, such as a cosmetic composition comprising at least one RMA. In one embodiment, the detector arrangement 110 comprises at least one light source for delivering light (e.g., visible light) to the area of skin, and a sensor for detecting light reflected from the area of skin. The light source may comprise any suitable light emitting device for illuminating the area of skin, for example, one or more LEDs. The light source may also be selected and arranged to provide an amount of illumination over the area of skin sufficient to detect and/or measure reflectance of light by the skin. Preferably, the light source(s), collectively, provide a substantially uniform distribution of light over the area of skin being imaged. The sensor may comprise any suitable components for detecting reflectance. For example, the sensor may be sensitive to an amount of reflected light in one or more wavelengths. Suitable sensors may include, for example, photographic or video cameras, photodiodes and/or phototransistors as would be understood by those skilled in the art.

The detector arrangement 110, including the light source and sensor are operably connected to a processing arrangement 130 to execute instructions stored on a computer-accessible medium 140. The processing arrangement 130 in this embodiment controls the light source and receives and analyzes imaging data received from the sensor. It is contemplated that the processing arrangement 130 and the computer-accessible medium 140 may be positioned anywhere within or external to the device 100. In one embodiment, as shown in FIG. 1, the processing arrangement 130 and the computer-accessible medium 140 are located within the handle portion 104. The processing arrangement 130 in this embodiment also controls the applicator arrangement 120 to selectively apply the composition to frexels at which artifacts are identified. The processing arrangement 130 may be, e.g., entirely or a part of, or include, but is not limited to, a computer/processor that can include, e.g., one or more microprocessors, and use instructions stored on a computer-accessible medium 140 (e.g., memory storage device). The computer-accessible medium 140 may, for example, be a non-transitory computer-accessible medium containing executable instructions therein. A storage arrangement may be provided separately from the computer-accessible medium 140, which may provide the instructions to the processing arrangement 130 to configure the processing arrangement 130 to execute certain exemplary procedures, processes and methods.

The applicator arrangement 120 according to this embodiment comprises at least one suitable composition application device for depositing a composition onto one or more frexels at which artifacts have been identified. An exemplary cosmetic application device in this embodiment may include, for example, a sprayer (e.g., an electronic sprayer or airbrush sprayer), a drop control device, or any other suitable application device for applying a composition in small drops to identified frexels as would be understood by those skilled in the art. In one exemplary embodiment, the applicator arrangement 120 comprises a nozzle for depositing a pressurized liquid or viscous composition in the form of a pressurized mist onto the skin to form a thin layer of cosmetic coverage at an identified frexel. The nozzle may be any suitable device for depositing a thin layer of the cosmetic composition onto the skin. In one exemplary embodiment, the nozzle may comprise dual chambers with a first chamber holding the liquid or viscous composition and a second chamber containing a propellant (e.g., compressed air or nitrogen gas) applying a pressure to, but not mixed with the composition when a pulse of the composition is dispensed to a frexel. In another example, the nozzle may comprise a first chamber holding the liquid or viscous composition and a second chamber containing a propellant to be mixed with the cosmetic composition when a pulse of the composition is dispensed to a frexel. Although two exemplary embodiments of the nozzle are described above, it is contemplated that the device of the present application may include any suitable nozzle for dispensing droplets of the composition under pressure as would be understood by those skilled in the art. In certain embodiments, the applicator arrangement 120 comprises multiple nozzles, such as, for example, an array of nozzles arranged in any desired configuration. The use of multiple nozzles increases an overall rate in which the device 100 may apply the composition to frexels, reducing a total amount of time a user will need to move the device 100 across a targeted portion of skin before the desired level of treatment of artifacts has been achieved. For example, the applicator arrangement 120 may include 3 to 8 nozzles, or 4 to 6 nozzles, each nozzle being aimed differently so that the composition can be applied to multiple frexels or different parts of a frexel at the same time. In one exemplary embodiment, the applicator arrangement 120 includes 5 nozzles.

The applicator arrangement 120 is operably connected to a reservoir 150 containing the composition to be applied to the skin. In particular, the applicator arrangement 120 is fluidly connected by a series of conduits, valves, and/or pressure sources to the reservoir 150. It is contemplated that the reservoir 150 may be housed anywhere within the device 100. In one exemplary embodiment, as shown in FIG. 1, the reservoir 150 is housed within the handle portion 104 of the device 100. The composition within the reservoir 150 is transferred from the reservoir 150 to the applicator arrangement 120 for deposition of the composition as will be described below. In some embodiments, the reservoir 150 is a removeable container that can be replaced upon exhaustion of the contents therein. For example, the reservoir 150 may be a pressurized canister containing the composition to be applied to the skin therein.

In one embodiment, the composition is a topical composition, as discussed above, that is applied to the skin to alter or minimize the appearance of an artifact based on the image data supplied by the detector arrangement 110. For example, the topical composition may be a cosmetic composition that reduce at least a portion of the magnitude of the artifact in the skin detected (e.g., intensity of spatial frequency components generating an undesired visual effect). In particular, the cosmetic composition may comprise at least one RMA, such as, for example, an opaque RMA having high refractive index particles. In one example, artifacts may be detected and quantified by analyzing a reflectance of the skin particularly in the middle spatial frequencies from the image data. It is believed that mitigating the appearance of regions of skin that exhibit reflectance within middle spatial frequencies, e.g., by applying a composition to modify the appearance and/or reflectance of skin and/or a composition that treats the skin to impart a healthier appearance to the skin, would modify or minimize the appearance of artifacts and improve the user's aesthetic appearance as described above.

The device 100 according to this embodiment further comprises a power source 160 for providing power to control and operate the device 100. It is contemplated that the power source 160 may be located anywhere within the device 100 or external to the device 100. In one exemplary embodiment, as shown in FIG. 1, the power source 160 which is housed within the handle portion 104 of the device 100 is operably connected to the detector arrangement 110, the applicator arrangement 120 and/or the processing arrangement 130. Those skilled in the art will understand that various known suitable sources of power may be used. For example, the power source 160 may comprise a battery or a connection to an external source of power. In particular, the power source 160 may comprise a rechargeable battery device.

As discussed above, the image data obtained by the detector arrangement 110 is analyzed by the processing arrangement 130 to identify artifacts and determine whether the applicator arrangement 120 should be triggered to apply the topical composition to any of the frexels within imaged the area of skin. Image data obtained by the detector arrangement 110 may be processed in any suitable manner to detect and/or quantify artifacts. Specifically, the image data may be processed to determine if one or more frexels in the imaged area represents an artifact whose appearance should be altered. In particular, the device 100 analyzes the image data to identify and locate artifacts according to a quantitative metric, such as, for example, as a percentage of a total intensity of light reflectance comprised of those spatial frequency components attributable to artifacts.

In an exemplary embodiment, spatial frequency components having middle spatial frequencies are used to identify and/or quantify artifacts in this embodiment. Those locations that include intense contributions in the middle spatial frequencies of an image may, for example, include artifacts whose appearance a user may wish to alter or minimize. The middle spatial frequencies are believed to contribute a small percentage (e.g., around 5%) to the overall spatial frequency of an image of skin and/or visual perception of the skin. However, it is believed that spatial frequency components within the middle spatial frequencies are particularly visually noticeable and therefore, disproportionally impact the perceived aesthetic appearance of the skin. Therefore, it is proposed to alter the appearance of skin by selectively applying cosmetic to frexels corresponding to details within the middle spatial frequencies of an image of the skin to impart an aesthetic pleasing appearance to the skin. It may be particularly beneficial to selectively alter or minimize the appearance of only those frexels that correspond to middle spatial frequencies to provide a visually noticeable aesthetic change to the appearance of skin while modifying only a limited number of frexels on the skin. Therefore, a reduced amount of composition may be applied to the skin while still providing an aesthetically noticeable improvement to the appearance of skin.

For example, image data obtained by the detector arrangement 110 for an area of skin is analyzed by the processing arrangement 130 to determine whether a frexel contained within the area includes spatial frequency components that fall within the range of middle spatial frequencies for the imaged area of skin. More particularly, a magnitude of the artifact may be quantified as a percentage of a total intensity of light reflectance comprised of spatial frequency components within middle spatial frequencies for the imaged area. Preferably, the range of middle spatial frequencies is determined for each frame based on the reflectance of the entire imaged area. Additional devices and methods for detecting artifacts using reflectance and analysis of middle spatial frequencies are described in, for example, U.S. Pat. Nos. 8,007,062, 9,020,184 and 10,092,082, the disclosures of which are incorporated by reference herein.

In one example, the processing arrangement 130 directs the applicator arrangement 120 to selectively deposit the composition to a frexel only when that frexel is determined to include an artifact having a magnitude exceeding a predetermined threshold. The applicator arrangement 120 may deposit an opaque cosmetic composition at any desired amount or any desired percentage level of opacity. In particular, the applicator arrangement 120 deposits on the skin, with a single pulse delivery, the composition at the desired percentage level of opacity. Typically, the composition may comprise a low opacity light cosmetic, and an amount of composition delivered may be adjusted based on the desired opacity. The term "opacity" as used herein refers to an amount of coverage the composition provides over a substrate (e.g., skin) surface. At 100% opacity, the composition would fully cover the skin such that the appearance of the substrate would be of the pure bulk color of the composition. At 0% opacity, the cosmetic would be perfectly transparent such that the appearance of the substrate would be of the pure skin color, without any contribution from the composition. For example, at 50% opacity, the composition would partially cover the skin such that the appearance of the substrate would be a 50-50 average of the composition and skin color.

The applicator arrangement 120 deposits on a frexel identified as representing an artifact an amount of opaque cosmetic composition sufficient to reduce the percentage skin artifact detected to a desired level (i.e., until a desired level of reflectivity in the middle spatial frequencies is obtained for the frexel). The degree of mitigation for each frexel identified as representing an artifact may be selected as a level of opacity that should be applied by the cosmetic composition to achieve a desired level of reflectance, e.g., a reflectance equal to an average level of reflectance in the remainder of the imaged area of skin including the frexel in question. For example, the degree of mitigation (e.g., lightening of dark spots on the skin) may be determined as an opacity of a cosmetic having a predetermined level of reflectance (or e.g., lightness) that should be applied to the skin to achieve a desired reflectance (e.g., an aim reflectance corresponding to an average level of reflectance within the remainder of the area around the frexel in question). More particularly, as an example, if an infinitely thick covering of a specific cosmetic reflects 80% of light, a targeted point on the skin reflects 70% of light, and the desired aim reflection for that point of skin is 71%, then the desired degree of reflectance modification, in this case, lightening, is 10%. In a simplistic linear model of opacity, which linearly correlates reflectance with opacity of the cosmetic composition, a 10% opacity covering of an 80% lightness cosmetic composition over a 70% lightness skin results in the desired reflection of 71% of light at the targeted point after application of the cosmetic composition. However, it is contemplated that other models of opacity, where reflectance may depend on reflectance along with other additional variables, such as for example, density and wavelength of the cosmetic composition, may also be used.

In a particular example, the applicator arrangement 120 deposits a fixed amount of a topical composition in a single pulse. The fixed amount of topical composition delivered in a single pulse may be selected to reduce the artifact magnitude by a desired coverage level when the pulse is applied to the skin. Therefore, the fixed single pulse of topical composition may impart a predetermined fixed level of opacity (and reflectance) with each pulse of the topical composition delivered to the skin. For example, the applicator arrangement 120 may be configured to deliver a fixed amount of the topical composition at 5% opacity for each pulse. For an artifact that may require application of the topical composition at 20% opacity, the topical composition may need to be layered onto the artifact with a least four pulses of the topical composition at 5% opacity each. Such layering may be applied by multiple passes of the head portion 102 over the artifact. However, if the artifact has a sufficiently large area that a single pulse of the topical composition does not fully cover an entire area of the artifact, more passes, and therefore, delivery of more pulses of topical composition, over the large area artifact may be needed to provide the desired layering of the topical composition spread over a larger spatial area on the skin.

Although this multi-pass layering may appear to be inefficient, it is believed that such a multi-pass strategy is important for providing a good aesthetic end result in a practical device. First, because each subsequent pass of the device 100 allows the detector arrangement 110 to measure reflectance after application of a layer of topical composition onto the skin from a previous pass, the device 100 provides a near real-time iterative feedback process between each pass that can reduce unpredictable variations in different regions of skin based on how such different regions interact with the topical composition. For example, different skin regions of the face may respond differently to application of a cosmetic composition and therefore, the level of reduction in appearance of a skin artifact may vary depending on the interaction of such skin regions with the cosmetic composition. As another example, application of a thin-layer of the cosmetic composition to areas of the skin of the face that may typically be more oily, e.g., the T-zone on the face, may impart a different level of change to the reflectance of the skin as compared to areas of the skin of the face that may typically be less oily, e.g., the cheeks on the face. Second, because an artifact may not have a shape that corresponds exactly to the shape of the thin layer formed from a single pulse of topical composition delivered by the applicator arrangement 120, multiple passes of the device 100 over the same artifact allow artifacts of various shapes and sizes to be suitably addressed through the deposition of multiple pulses of composition during multiple passes. The iterative feedback provided during these multiple passes allows for adjustments to the selective application of the topical composition as the device is moved across the surface of the skin, and therefore, provides an overall broadened shape for the total deposition of topical composition to fit a larger spot having an artifact.

Figure 2:
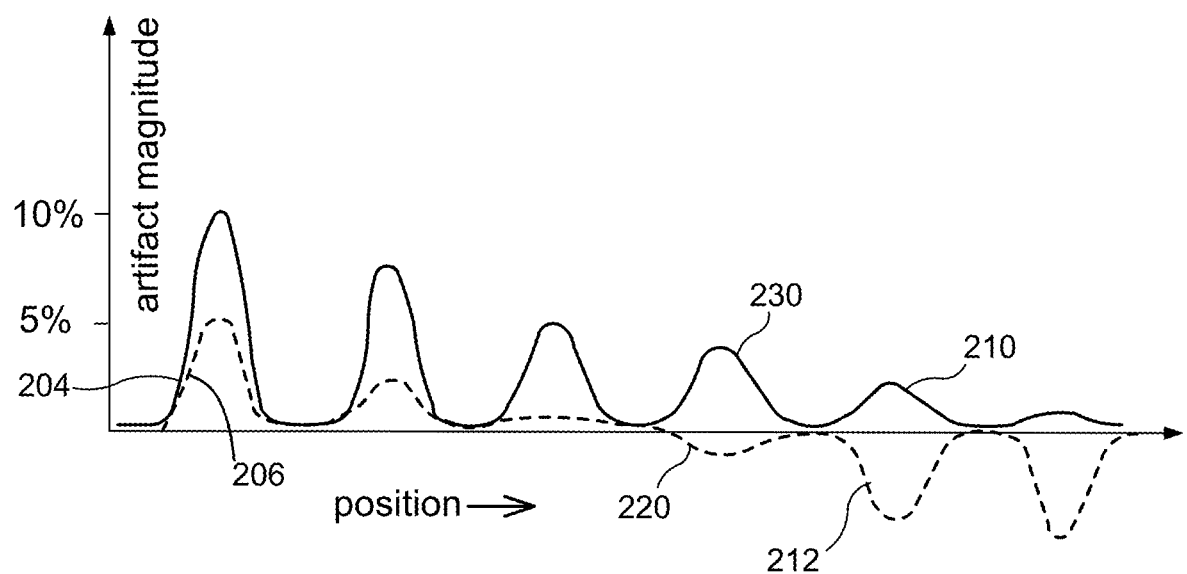
FIG. 2 shows an exemplary graphical representation of magnitudes of skin artifact detected over different positions along an exemplary length on the skin of the user, and the magnitudes of skin artifact after an exemplary application of a cosmetic composition.

As further explained below and illustrated in FIG. 2, the applicator arrangement 120 may, for example, selectively deposit a fixed amount of topical composition in a single pulse to a frexel when the device 100 determines that an artifact magnitude of the frexel exceeds a predetermined threshold. Such selective application of the topical composition may be particularly useful for artifacts having a lower end of artifact magnitude, such as, for example an artifact having a magnitude of skin defect of 5% or less. However, it is contemplated that such selective application of the topical composition may be used on artifacts having any magnitude of skin defect. FIG. 2 shows an exemplary graphical representation of the magnitudes of skin artifact (e.g., percentages of skin artifact) detected over different positions along an exemplary length on the skin of the user. The solid line represents magnitudes of skin artifact detected prior to application of any cosmetic composition. As can be seen in FIG. 2, several artifacts 204 are present along the exemplary length of skin. The dashed line 206 represents magnitudes of skin artifact after uniform application of a fixed amount of cosmetic composition selected to impart a reduction of the magnitude of skin defect by 5% ("5% cosmetic application") along the exemplary length of skin. As shown in FIG. 2, the 5% cosmetic application to an area of skin having a 4% skin artifact (pre-application artifact shown as 230, after cosmetic application shown as 220) may overcorrect the appearance of skin by 1%. FIG. 2 also show that the 5% cosmetic application to an area of skin having only a 2% skin artifact (pre-application artifact shown as 210, after cosmetic application shown as 212) may overcorrect the appearance of skin by 3%, which deviates further from a complete reduction of artifacts and therefore, do more damage than benefit to the aesthetic appearance of skin. In some examples, the predetermined threshold may be at a 0.80 of pulse opacity, meaning that the predetermine threshold is set at 80% of the level the fixed amount of cosmetic composition is selected to reduce when applied to the skin—i.e., a 4% skin artifact threshold for the 5% cosmetic application. By setting this predetermined threshold, the device 100 would operate to tolerate a 1% overcorrection of 4% skin artifact.

Figure 3:
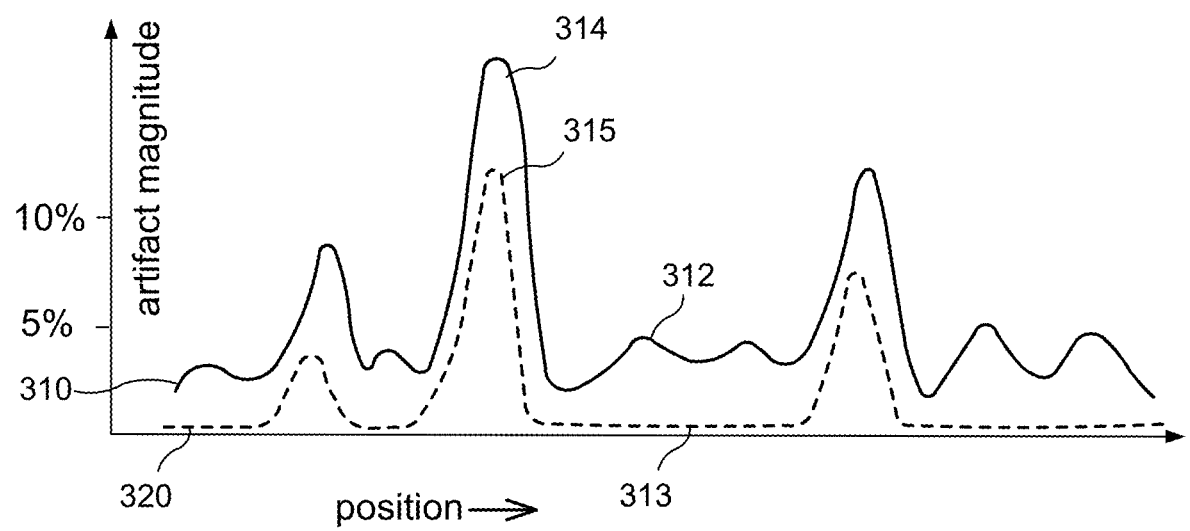
FIG. 3 shows another exemplary graphical representation of magnitudes of skin artifact detected over different positions along a different exemplary length on the skin of the user, and the magnitudes of skin artifact after another exemplary application of a cosmetic composition.

A thin layer of a topical composition may be applied to those frexels identified as having artifacts that exceed the predetermined threshold on each pass. Artifacts having magnitudes that are just above the predetermined threshold may be substantially or completely reduced on the first pass. However, artifact having magnitudes that are well in excess of the predetermined threshold may not be sufficiently mitigated by the fixed amount of topical composition delivered in a single pulse, which has a fixed pulse opacity. The effect of this limitation is further shown in an exemplary graphical representation in FIG. 3, which provides another exemplary graphical representation of the magnitudes of skin artifacts detected over different positions along a length on the skin of the user. The solid line 310 represents magnitudes of skin artifacts detected prior to application of any cosmetic composition. As can be seen in FIG. 3, an artifact having a smaller magnitude 312 and another artifact having a larger magnitude 314 are present along the exemplary length of skin. The dashed line 320 represents magnitudes of skin artifacts after repeated application, for a very large number of passes across the exemplary length of the skin, of a very small fixed amount of cosmetic composition set to have a low opacity at each pulse that is triggered by a low predetermined threshold value. Because of the low threshold for triggering application of the cosmetic composition to the skin, almost every region of skin, for example, about half of the frexels, may exceed the low predetermined threshold value and trigger application of a small pulse of the cosmetic composition. After a sufficient number of these low threshold passes achieve a target level of total opacity, for example, a 5% cosmetic application, which is shown by the dashed line 320 in FIG. 3, all artifacts having a magnitude less than 5%, such as, for example, the artifact shown at 312, will have been substantially or completely mitigated by the cosmetic composition applied to the skin, as shown at 313. This may result in almost every area of the skin being covered with a thin coating of cosmetic, while artifacts having a larger magnitude, such as, for example, that shown at 314, cannot be sufficiently mitigated by a 5% cosmetic application, as shown at 315, but are instead reduced in magnitude by 5%.

Repeated application of very small fixed amounts of a topical composition having low opacity does not provide an ideal visually pleasing aesthetic appearance to the skin. Instead, in areas of the skin where there are low levels of artifact magnitudes, coverage by the composition using the above describe parameters may impart an appearance that is smoothed too much resulting in an artificial/unnatural appearance of the skin. Meanwhile, artifacts having greater magnitudes may not be sufficiently reduced. In addition, such repeated applications of small fixed pulses of topical composition triggered at each location exceeding a low predetermined threshold may result in a greater total amount of the composition being applied to the skin, e.g., almost every area of skin may receive at least a small amount of the composition. Therefore, the composition may form a continuous thin film covering almost the entire surface of the skin, resulting in a less natural feel for the skin.

Thus, it is best to select suitable predetermined thresholds and amounts of topical composition to be applied to the skin during each pass that do not suffer from the deficiencies discussed above—in particular, to better reduce the appearance of artifacts by applying more of the composition to a smaller number of more visible artifacts. Therefore, it may be useful to selectively target application of the topical composition to a smaller number of frexels that have an outsized contribution to the aesthetic appearance of the skin. In one exemplary embodiment, the device 100 selectively applies a cosmetic composition to the skin to mimic patterning observed in textured mediums, such as, for example, oil paintings on canvas. It appears that such background texturing reduces the need for perfection in an image. In particular, a small amount of noise in such images seems to prevent the human visual system from seeing artifacts below a threshold of the background pattern or noise. This may explain the popularity of using a textured cloth canvas for artistic painting. The canvas may provide a continuous and uniform pattern that obviates a need for details that are weaker than the pattern of the canvas. Painting on smooth surfaces is sometimes done, especially when intricate detail is to be revealed in the artist's work. However, this level of intricate detail may be avoided by when the image is masked by the texture of canvas and brush strokes. It has been observed that photographs that print on textured or canvas mediums reduce a need for perfection in the photograph, without appearing imperfect to typical observers.

Similarly, it has been observed that the amount of conventional makeup applied to the skin does not significantly change visual perception of a user's aesthetic appearance, e.g., perceived age of the user. It is believed that this result may be in part because conventional makeup is applied as a continuous thin film, and therefore, smooths over the entirety of the skin. When a natural and uniform pattern is left on the skin while high magnitude artifacts are substantially reduced, the eye may be satisfied that the perceptual volume is correct as is. The eye does not seem to readjust the perceptual volume of artifacts in response, but instead seems to perceive a more flawless, younger skin. The skin's natural, faint and uniform visual patterns appear to be sufficient to induce a perceptual response similar to that of the canvas and brush strokes in paintings.

The device 100 operates in a manner that incorporates the theory discussed above by selectively applying topical composition only to frexels at which artifacts of high magnitude are identified while refraining from applying the composition to other frexels to allow the natural patterns of the skin to show through to generate a perception of younger and/or less flawed skin. The threshold level, and degree of background pattern smoothing, are aesthetic choices without a precise quantitative definition as what is aesthetically pleasing look for skin is a matter of taste. However, it is understood that total coverage of the skin by a cosmetic and/or total smoothing of an appearance of skin is rarely the most desirable.

Figure 4:
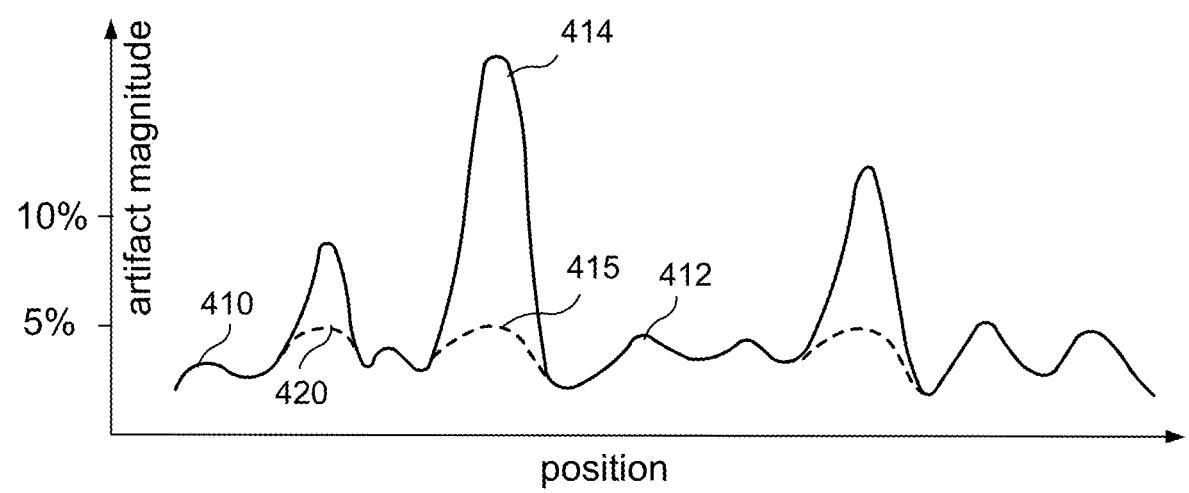
FIG. 4 shows a further exemplary graphical representation of magnitudes of skin artifact as shown in FIG. 3, and the magnitudes of skin artifact after an alternative exemplary application of a cosmetic composition.

FIG. 4 provides another exemplary graphical representation of magnitudes of skin artifacts (e.g., percentages of skin artifact) detected over different positions along a length on the skin of the user. The solid line 410 corresponds to the solid line 310 of FIG. 3, which represents magnitudes of skin artifacts detected prior to application of any cosmetic composition. Similar to FIG. 3, FIG. 4 also includes an artifact having a smaller magnitude 412 and another artifact having a larger magnitude 414 along the exemplary length of skin. The dashed line 420 represents magnitudes of artifacts after repeated application of fixed pulses of cosmetic composition triggered when the predetermined threshold level exceeds the predetermined coverage level to be obtained by a fixed pulse of cosmetic composition (e.g., the level of artifact reduction imparted by application of the fixed amount of the cosmetic composition to the skin). As can be seen in FIG. 4, portions of the dashed line 420 is coincident or substantially coincident to the solid line 410, demonstrating that cosmetic composition is either not applied or applied minimally to those portions. The predetermined threshold value in this example is set a level close to a level of artifact magnitude corresponding to a background pattern (e.g., variations, preferably substantially uniform variations, within 5% skin artifact). The device 100 may be moved by a user back and forth across the skin in multiple passes until the completion—i.e., when a desired aesthetic appearance is achieved, or when the application of the composition has rendered the artifact magnitude of all of the previously detected artifacts below the predetermined threshold. The resulting percentages of skin artifact are, for example, illustrated as the dashed line 420 in FIG. 4. As can be seen in FIG. 4, the artifacts, such as 414, may be mitigated in the manner described herein such that they are hidden in the natural, continuous patterns of the skin 415. It is believed that the eye perceives the remaining contours with of artifact magnitudes within range of the continuous pattern of the skin as healthy and natural even though only a relatively low or imperceptible amount of cosmetic composition has deposited on the skin.

In a particular embodiment, the device 100 may operate in at least two different modes. Each mode of the device 100 may deposit a predetermined fixed amount of the topical composition in a single pulse in response to a frexel having an artifact magnitude that exceeds a predetermined threshold. In a first mode, the device 100 delivers a fixed amount of topical composition in a single pulse to a frexel only when the frexel has an artifact magnitude that exceeds a first predetermined threshold. The first predetermined threshold is selected to exceed the level of artifact reduction imparted by application of the fixed amount of the topical composition to the skin. The device 100 may operate in the first mode initially and continue to operate in this mode for a certain amount of time before transitioning to a second mode. In the second mode, the device 100 delivers the same fixed amount of topical composition in a single pulse to a frexel only when the frexel has an artifact magnitude that exceeds a second predetermined threshold. The second predetermined threshold is selected to be lower than the first predetermined threshold. Preferably, the second predetermined threshold is also selected to exceed the predetermined coverage level to be obtained by a fixed pulse of topical composition. Starting with a higher threshold in the first mode allows the device 100 to target application of the topical composition first to those artifacts having higher magnitudes without treating frexels having artifact magnitudes in the range of that comprising a background pattern of natural skin. Subsequent application of the topical composition using a lower threshold in the second mode allows the artifact magnitudes of the background pattern to be reduced to a preferred and controlled degree—i.e., a preferred magnitude of skin artifact. If the device operated only in the second mode at the lower threshold for the duration of a session of use, components of the background pattern at or above this lower threshold would be covered by the topical composition before the artifacts having higher magnitudes were reduced by application of the cosmetic composition. Therefore, to reach a substantially complete or complete reduction of the high magnitudes artifacts using only the second mode would result in complete coverage of the desirable background pattern of natural skin.

The transition from the first mode to the second mode may be manually triggered by the user, for example, by providing a user input using via a user interface 170. The user interface 170 is operably connected to the processing arrangement 120 to enable the user to manually signal to the processing arrangement 120 that the predetermined threshold value should be adjusted. Exemplary embodiments of the user interface 170 may include, a toggle button, a touch screen, a switch, etc. Alternatively, the device 100 may automatically transition from the first mode to the second mode when a predetermined criterion is satisfied. For example, as magnitudes of artifacts are reduced by depositing the topical composition to those particular areas via multiple passes of the device 100 across the skin, the device 100 may deposit pulses of topical composition with less frequency as frexels having higher magnitudes of artifact become covered with the topical composition. Therefore, the device 100 may automatically transition from the first mode to the second mode when a deposition rate of the applicator arrangement 120 falls below a predetermined rate. By transitioning from the first mode to the second mode, the processing arrangement 130 will likely increase the rate at which the applicator arrangement 120 deposits pulses of topical composition as more frexels will be in the range to be treated.

It is contemplated that additional modes operating at additional predetermined threshold values may be also be used. Additional modes utilizing predetermined threshold values selected to be lower than that of the predetermined threshold of a prior mode are also contemplated by the present application. In some embodiments, the additional predetermined threshold values may also be in excess of the predetermined coverage level of artifact reduction imparted by the fixed amount of the topical composition when applied to the skin.

In another embodiment of the present application, the device 100 may dynamically adjust the threshold value of the magnitude at which artifacts are treated. The dynamically adjusted threshold value may be initially selected to be any suitable value that exceeds the level of artifact reduction imparted by application of the fixed amount of topical composition to the skin. The device 100 may continuously or periodically adjust the threshold value based, for example, on a deposition rate of the applicator arrangement 120. The threshold value may be dynamically adjusted to maintain a substantially constant deposition rate (e.g., within a standard deviation, within ±5%, within ±3%, within ±2% or within ±1% of the deposition rates over time). For example, in a system where flow capability may be limited by a compressor, this dynamically adjusted threshold may be adjusted to allow the device 100 to maintain a substantially constant deposition rate, while operating below the device's hardware maximum limitations, by increasing the dynamically adjusted threshold and thereby adjusting to the changing operating parameters of the device, without forcing the user to stop use of the device 100 before a desired aesthetic appearance is reached. The deposition rate of the applicator arrangement 120 may be determined as pulses per unit of time. Alternatively, the deposition rate may be determined as pulses per unit of distance traveled by the device 100 across the skin to compensate for variability in the speed at which a user manually moves the device 100 across the skin.

The device 100 may also adjust the amount of topical composition deposited in a single pulse. For example, the exiting pressure of the applicator arrangement 120 may be adjusted to modify the amount and/or opacity of the topical composition deposited onto the skin. Such a changing amount of topical composition, in particular a cosmetic composition, delivered in each pulse may alter the opacity delivered via each pulse. It is believed that when the opacity doubles, the topical composition usage rate and speed of application for the equivalent aesthetic benefit may also double. The increased opacity may also increase randomness in the magnitudes of artifact that remain after continuous use of the device 100 in multiple passes. For example, the device 100 may be adjusted to deliver a pulse of cosmetic composition at 10% cosmetic application. This increased amount of cosmetic composition may increase opacity of the cosmetic composition delivered at each pulse. The 10% cosmetic application may be deposited onto frexels that have an artifact magnitude exceeding a 10% threshold. Therefore, in this example, an 18% artifact may be reduced to an 8% artifact with application of a single pulse of cosmetic composition, while a 22% artifact may be reduced to a 2% artifact with two pulses. It is believed that this increase in randomness will not significantly affect perceived quality of the skin because each pass of the device 100 provides a near real-time iterative feedback process that allows for adjustments based on the appearance of skin after each application of topical composition to the skin. However, an increase in speed and therefore, reduction in a total amount of time needed for continuous multiple passes before completion may be desired.

Figure 5:
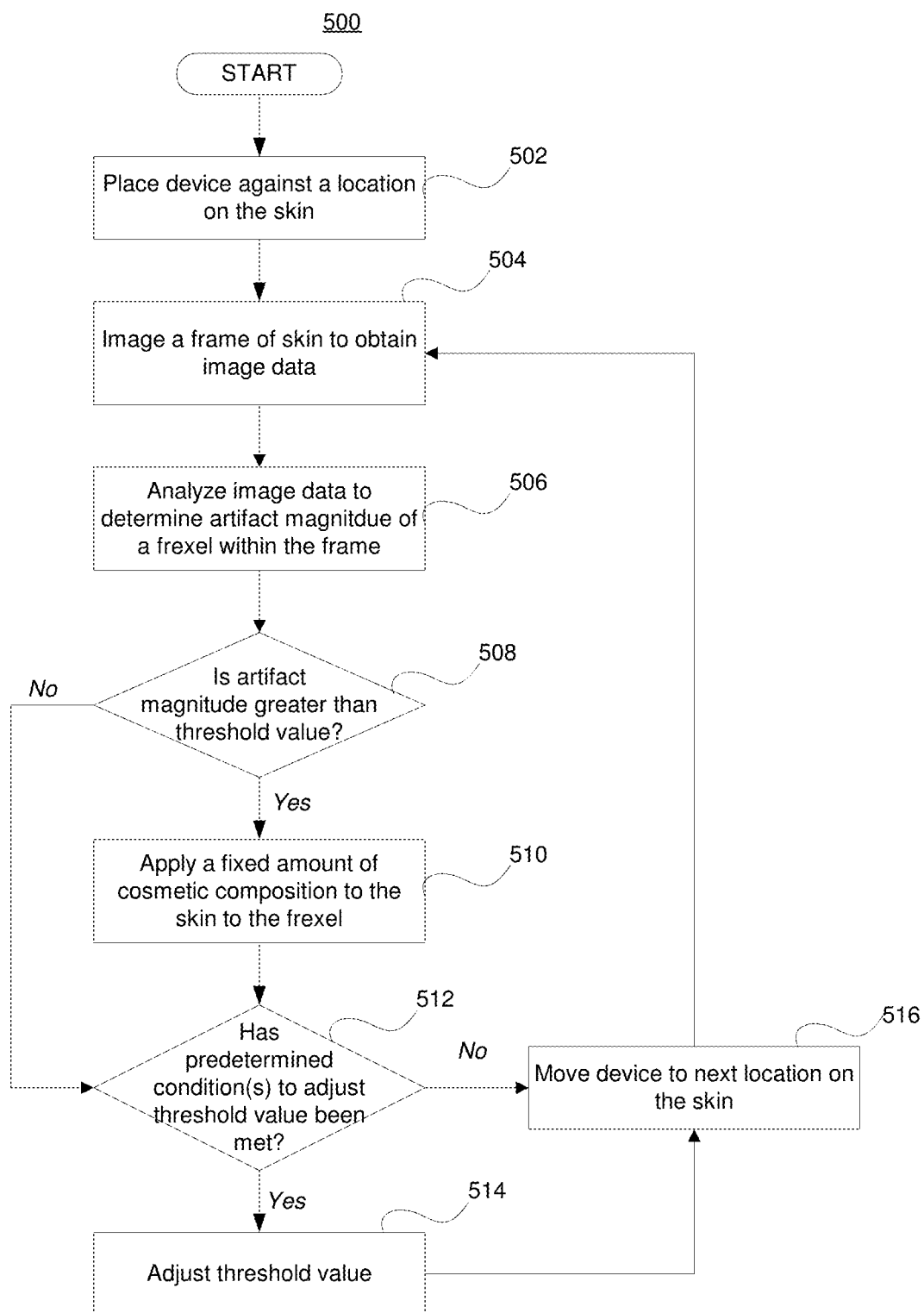
FIG. 5 shows an exemplary method for selectively applying a topical composition to the skin of a user, according to an exemplary embodiment of the present application.

The present application also includes a method for selectively applying a topical composition to the skin. An exemplary method 500 is show in FIG. 5. In step 502, the user may initiate use of the device 100 by placing a head portion 102 of the device 100 against a surface of a skin, in particular, the skin of the face. The head portion 102 may cover an area of skin, e.g., an area constituting a frame to be imaged and analyzed by the device 100. As indicated in step 504, the device 100 may sense and/or image the area of skin over which the device 100 is positioned to obtain image data, as discussed above. In step 506, the device 100, in particular, the processing arrangement 130, analyzes the image data to determine an artifact magnitude for one or more frexels in the imaged portion of skin. In step 508, the artifact magnitude is compared to a predetermine threshold value to determine whether a topical composition should be applied to the frexel. In particular, when the magnitude of the frexel exceeds the threshold value, then the method 500 proceeds to step 510. Otherwise, the method 500 will not apply the topical composition to the frexel and instead proceeds to step 512, as discussed further below.

In step 510, the applicator arrangement 120 deposits a fixed amount of topical composition to the frexel. Subsequently, the method 500 moves to step 512, which determines if one or more predetermined condition(s) have been met for modifying the threshold value used in step 508 (e.g., upon receipt of input from the user or when the deposition rate falls below a predetermined rate). The predetermined condition(s) may include any one or more criteria for triggering a modification to the threshold value used in step 508. For example, as discussed above, the predetermined condition(s) may comprise receiving a manual input from a user via a user interface or when a deposition rate of the applicator arrangement falls below a predetermined rate (e.g., a predetermined number of pulses per second or a predetermined number of pulses per distance), as discussed above. The predetermined condition(s) can also require the device 100 to adjust the predetermined threshold value when the device is operating at or near any one or more of its hardware maximum limitations. Furthermore, it is contemplated that changes to other operating parameters of the device 100 may also be used as predetermined condition(s) for triggering a modification to the threshold value. If the predetermined condition(s) are met, the method 500 proceeds to step 514 where the threshold value used in step 508 is modified. If the predetermined condition(s) have not been met, the device 100 may be moved by the user to a new frame or area of the skin (step 516), without any changes in the threshold value. This movement may be detected by the device 100 by any suitable means, such as, for example, an accelerometer or image analysis. The method 500 then returns to step 504 and images, analyzes, and selectively applies topical composition, as determined by the device 100, to this new area of skin in the same manner described above. It is noted that the method 500 may be interrupted and terminated by the user before any one of steps 502 through 516 by any suitable operation, such as, for example, removing the device 100 from the skin or switching off the device 100, in particular, the power source 160 of the device.

In certain embodiments, step 512 may not be necessary. Instead, the threshold value may be continually updated through each iteration of the method 500. The threshold value may be a dynamically adjusted threshold, as discussed above.

Those skilled in the art will understand that the exemplary embodiments described herein may be implemented in any number of manners, including as a separate software module, as a combination of hardware and software, etc. For example, the exemplary methods may be embodiment in one or more programs stored in a non-transitory storage medium and containing lines of code that, when compiled, may be executed by one or more processor cores or a separate processor. A system according to one embodiment comprises a plurality of processor cores and a set of instructions executing on the plurality of processor cores to perform the exemplary methods discussed above. The processor cores or separate processor may be incorporated in or may communicate with any suitable electronic device, for example, on board processing arrangements within the device or processing arrangements external to the device, e.g., a mobile computing device, a smart phone, a computing tablet, a computing device, etc., that may be in communications with at least a portion of the device.

EXAMPLES

Example I

In Example I, an exemplary device is simulated to operate in two modes, as described above: a first mode having a threshold value at 14% skin artifact; and a second mode having a threshold value at 6% skin artifact, after the higher threshold passes from the first mode had reached completion to achieve a more natural look. The simulation is performed by starting with an uncorrected image of a region of skin under even lighting, analyzing image data corresponding to the image to determine an artifact magnitude for each frexel within the image, and simulating continuous application of pulses of a cosmetic composition across all the frexels across the face in the image, as specified above.

Figure 6:
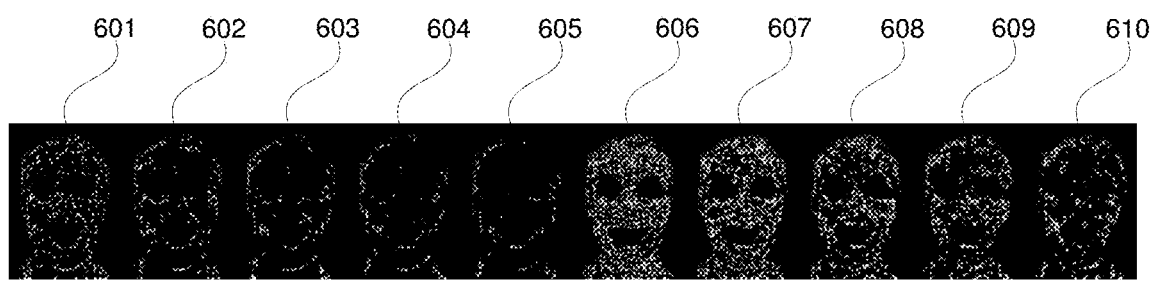
FIG. 6 shows exemplary deposition patterns over time of an exemplary device operating in the manner describe in Example I herein, where the deposition pattern for a first pass of the device is shown at the left and the deposition pattern for a last pass of the device is shown at the right.

The transition between the first mode to the second mode of Example I is illustrated in FIG. 6, which shows exemplary deposition patterns over time of the exemplary device operating in the manner describe above for Example I. It is noted that the simulated deposition patterns shown in FIG. 6 are masked with respect to the hair, mouth and eyes, which corresponds to an exemplary manner in which a user could move the device 100 across the skin of the face in multiple passes and avoid application of the cosmetic composition onto the hair or into the mouth and eyes. FIG. 6 shows the first pass at the left 601 of the figure and the last pass at the right 610. The intervening patterns between the first pass 601 and the last pass 610 are sequentially labeled as images 602 to 609. Midway through the deposition patterns shown in FIG. 6, in particular between images 605 and 606, the device transitioned from the first mode to the second mode and thereby reducing the threshold value from 14% artifact to 6% artifact for triggering deposition of cosmetic composition onto the skin. As can be seen in FIG. 6, the rate of deposition initially decreased over time. The rate of deposition may reach zero when all artifacts above the threshold have been mitigated. As shown in the left half of FIG. 6 (images 601 to 605), deposition of cosmetic composition may be halted for the majority of the skin. The remaining visible pulses near the middle of FIG. 6 correspond to areas having an extremely high magnitude of artifact, such as hair that would not likely be covered even after repeated deposition of the cosmetic composition. FIG. 6 also shows that when the exemplary device transitions from the first mode to the second mode where the threshold value is reduced to 6% artifact, the deposition rate subsequently increases, and eventually in the later passes, the deposition rate falls again as the 6% artifact is satisfied by multiple passes of the device.

Example II

Figure 7:
FIG. 7 shows an exemplary control image of a region of skin from a face of a subject without any application of a cosmetic composition.

The aesthetic effects of different methods for selectively applying a cosmetic composition to the skin are demonstrated in FIGS. 7 to 13. FIG. 7 shows a control image of a region of the skin on the face of a subject without any simulated application of a cosmetic composition. Each of FIGS. 8 to 13 shows the same region of skin of the same subject simulated in a manner similar to Example I under different methods for selectively applying a cosmetic composition (e.g., applying different limits and/or thresholds). It is noted that the images of FIGS. 8, 10 and 12 were captured in a green channel and the green channel images were further processed to improve image contrast.

Figure 8:
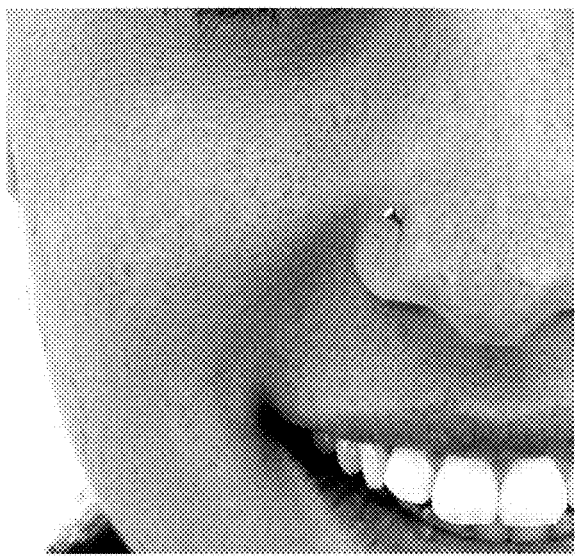
FIG. 8 shows an exemplary image of the same region of skin from the subject of FIG. 7, where middle spatial frequencies are simulated to be reduced in the manner described in Example I.
Figure 9:
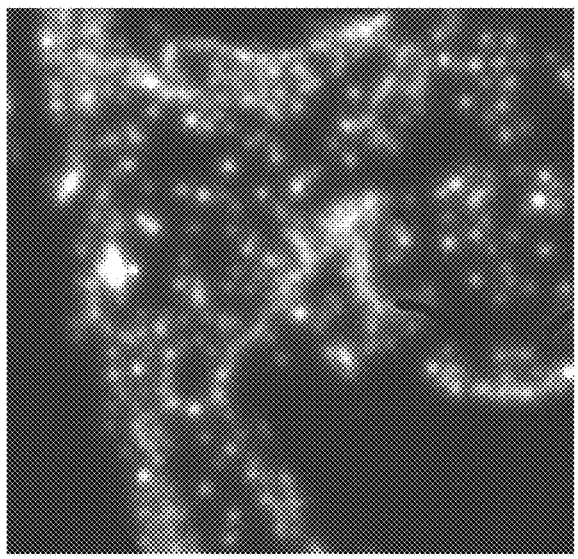
FIG. 9 shows a distribution of pulses of cosmetic composition simulated to be applied to the region of skin in FIG. 8.

FIG. 8 shows a simulated image using the method describe above in Example I. As can be seen, the image in FIG. 8 shows a natural aesthetic appearance while being able to utilizes delivery of fixed pulses of cosmetic composition over multiple passes across the skin. FIG. 9 shows a distribution of the pulses simulated to be applied in FIG. 8. Notably, FIG. 8 shows a noticeable improvement to the aesthetic of skin, while FIG. 9 shows that pulses of cosmetic, as simulated in FIG. 8, would be selectively applied only to selected regions of the skin and therefore, would reduce the total amount of cosmetic needed to impart an improved aesthetic appearance to the skin.

Figure 10:
FIG. 10 shows an exemplary image of the same region of skin from the subject of FIG. 7, where middle spatial frequencies are simulated to be reduced for skin artifacts having magnitudes less than a predetermined limit.
Figure 11:
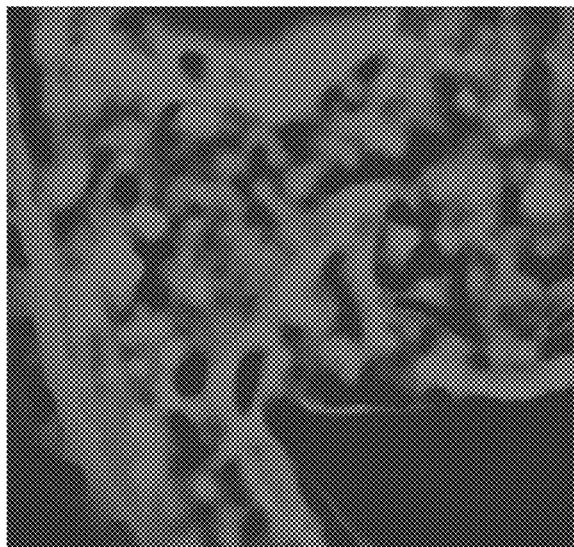
FIG. 11 shows a distribution of pulses of cosmetic composition simulated to be applied to the region of skin in FIG. 10.
Figure 12:
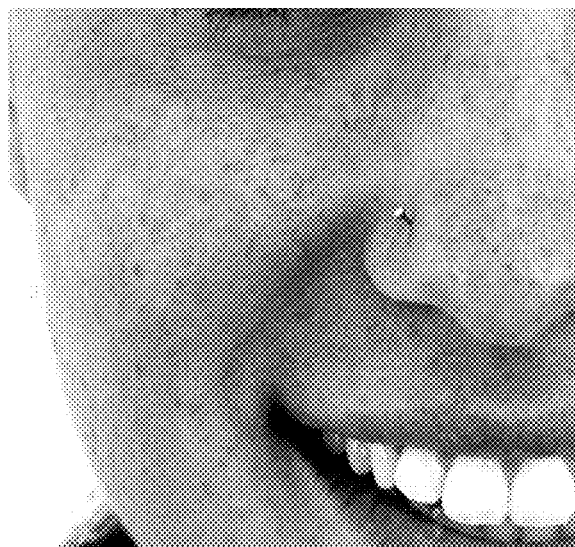
FIG. 12 shows an exemplary image of the same region of skin from the subject of FIG. 7, where middle spatial frequencies are simulated to be reduced for skin artifacts having magnitudes greater than 10% skin artifact and less than the predetermined limit of FIG. 10.

FIGS. 10 through 12 illustrate the aesthetic difference between a device operating in low and high threshold modes, respectively.

In FIG. 10, the middle spatial frequencies of the image are reduced up to a predetermined limit of 5% artifact. Specifically, the middle spatial frequencies of each frexel were determined as discussed above and a calculated level of correction to the middle spatial frequencies were simulated for frexels having less than 5% skin artifact, i.e., below the predetermined limit. FIG. 11 shows a distribution of the pulses simulated to be applied in FIG. 10. As can be seen in FIG. 10, the simulated image shows an unnatural looking smoothness to the skin, but particular artifacts remain noticeable within the overall aesthetic appearance of the skin. In addition, as shown in FIG. 11, the aesthetic appearance simulated in FIG. 10 requires depositing a large number of pulses with a very faint amount of cosmetic composition in each pulse. Therefore, when in actual use, would deposit cosmetic composition all over the skin over multiple passes across the skin.

Figure 13:
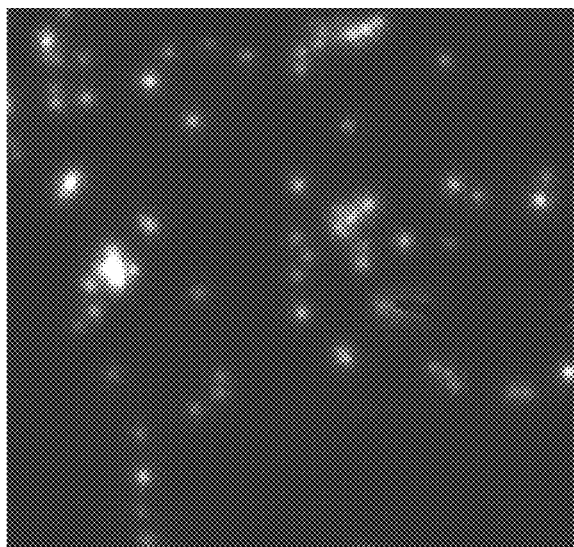
FIG. 13 shows a distribution of pulses of cosmetic composition simulated to be applied to the region of skin in FIG. 12.

In FIG. 12, the artifacts are identified using middle spatial frequencies and a calculated level of correction to the middle spatial frequencies were simulated in a manner similar to that of FIG. 10. However, in FIG. 12, a 10% artifact threshold is used such that the corrections are only applied to frexels having an artifact magnitude of greater than 10% artifact. As can be seen in FIG. 12, a background pattern below 10% artifact is retained on the skin in this image, but that stronger artifacts above 10% are reduced to the level of that pattern, so they are no longer visually distinguishable from the background pattern of the skin. It is noted that the original image shown in FIG. 7 includes high magnitude artifacts and these artifacts are not aesthetically noticeable in the image shown in FIG. 12. FIG. 13 shows a distribution of the pulses simulated to be applied in FIG. 12. As shown in FIG. 13, the image shown in FIG. 12 imparts an improvement to the aesthetic appearance of skin while using a minimum amount of the cosmetic composition and skin area coverage. Therefore, this example is simulated to apply significantly fewer corrections to the skin for a cleaner appearance while using less cosmetic composition.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method for selectively applying a composition to smooth appearance of a treatment surface of a subject, comprising:
   (i) analyzing, by a processing arrangement, image data corresponding to an imaged area of the treatment surface to determine an artifact magnitude of a location within the imaged area of the treatment surface;
   (ii) comparing, by the processing arrangement, the artifact magnitude of the location to a threshold value; and
   (iii) applying, by an applicator arrangement, a fixed amount of the composition to the location only when the artifact magnitude of the location exceeds the threshold value, wherein the fixed amount of the composition reduces the artifact magnitude by a fixed coverage level, the fix coverage level is less than the threshold value;
   (iv) repeating steps (i) through (iii) for a subsequent area of the treatment surface until a manual input is received from the subject via a user interface, the manual input indicating the subject desires further smoothing of the appearance of the treatment surface;
   (v) reducing the threshold value upon receiving the manual input, the reduced threshold value being greater than the fix coverage level; and
   (vi) repeating steps (i) through (v) for next areas of the treatment surface until a manual interruption is received from the subject.

2. The method of claim 1, wherein the subject is human, the treatment surface is skin of the subject.

3. The method of claim 2, wherein the treatment surface is skin on a face of a human.

4. The method of claim 1, wherein the artifact magnitude is determined based on a reflectance of the imaged area of the treatment surface.

5. The method of claim 4, wherein the artifact magnitude is determined as a percentage of light reflectance of the location that comprises spatial frequency components within middle spatial frequencies for the imaged area of the treatment surface.

6. The method of claim 1, wherein the composition is a cosmetic composition.

7. The method of claim 1, wherein the composition comprises a reflectance modifying agent.

8. The method of claim 1, wherein the composition comprises an active ingredient for treating a skin condition.

9. A handheld device for selectively applying a composition to a treatment surface, comprising:
   an applicator arrangement applying a fixed amount of the composition to the treatment surface;
   a detector obtaining image data corresponding to an image of an area of the treatment surface;
   a user interface for obtaining from a manual input from a user; and
   a processing arrangement analyzing the image data to determine an artifact magnitude of a frexel within the area of the treatment surface, the processing arrangement directing the applicator arrangement to apply the fixed amount of the composition to the frexel when the artifact magnitude of the frexel is greater than a threshold value,
      wherein the fixed amount of the composition reduces the artifact magnitude by a fixed coverage level, and the fix coverage level being less than the threshold value,
      wherein the threshold value is reduced by the processing arrangement when the user interface receives the manual input, and the reduced threshold value being less than the threshold value, and
      wherein the processing arrangement directs the applicator arrangement to apply the fixed amount of the composition to a frexel in a next area of the treatment surface when an artifact magnitude of the frexel in the next area of the treatment surface is greater than the reduced threshold value.

10. The handheld device of claim 9, wherein the treatment surface is human skin.

11. The handheld device of claim 10, wherein the treatment surface is skin on a face of a human.

12. The handheld device of claim 9, wherein the composition is a cosmetic composition.

13. The handheld device of claim 9, wherein the composition comprises a reflectance modifying agent.

14. The handheld device of claim 9, wherein the composition comprises an active ingredient for treating a skin condition.

15. The handheld device of claim 9, wherein the detector arrangement comprises a light source for delivering light to the area of the treatment surface, and a sensor detecting light from the area of the treatment surface to obtain the image data.

16. The handheld device of claim 9, wherein the artifact magnitude is determined based on a reflectance of the treatment surface detected in the image.

17. The handheld device of claim 16, wherein the artifact magnitude is determined as a percentage of light reflectance of the frexel within the imaged area of the treatment surface.

18. The handheld device of claim 16, wherein the artifact magnitude is determined as a percentage of light reflectance of the frexel that comprises spatial frequency components within middle spatial frequencies for the imaged area of the treatment surface.

19. The handheld device of claim 9, wherein the user interface is a toggle button or a switch.

* * * * *